United States Patent [19]

Mizutani

[11] 4,313,163

[45] Jan. 26, 1982

[54] APPARATUS FOR CONTROLLING A TOMOGRAPH DISPLAY

[75] Inventor: Hiroyuki Mizutani, Yokohama, Japan

[73] Assignee: Tokyo Shibaura Denki Kabushiki Kaisha, Japan

[21] Appl. No.: 112,453

[22] Filed: Jan. 16, 1980

[30] Foreign Application Priority Data

Jan. 22, 1979 [JP] Japan ................................. 54-4760

[51] Int. Cl.[3] .......................................... G01J 23/00
[52] U.S. Cl. ............................. 364/414; 250/445 T; 364/577
[58] Field of Search .......................... 364/414, 577; 250/445 R, 445 T

[56] References Cited

U.S. PATENT DOCUMENTS

| | | | |
|---|---|---|---|
| 4,064,393 | 12/1977 | Pasedach et al. | 364/414 |
| 4,149,259 | 4/1979 | Kowalski | 364/414 |
| 4,189,775 | 2/1980 | Inouye et al. | 250/455 T |
| 4,205,375 | 3/1980 | Inouye et al. | 250/445 T |
| 4,211,926 | 7/1980 | Nakaya et al. | 250/445 T |

Primary Examiner—Errol A. Krass
Attorney, Agent, or Firm—Finnegan, Henderson, Farabow, Garrett & Dunner

[57] ABSTRACT

An apparatus for generating a tomographic display projects X-ray beams in a fan-shaped array through a subject in many directions within a plane, detects how much each X-ray has been absorbed by the subject, and obtains the X-ray absorption coefficient of a given point of the subject existing within the plane. X-ray absorption data are back-projected onto a reference line existing in the plane are accumulated in the pixels defining the subject under examination, are distributed onto said given point of the subject, to obtain the distribution of X-ray absorption coefficients in said plane of the subject.

9 Claims, 13 Drawing Figures

APPARATUS FOR CONTROLLING A TOMOGRAPH DISPLAY

This invention relates to an apparatus for controlling a tomograph display using radiation, particularly an X-ray fan beam.

A computed tomography apparatus has long been known, which provides a tomograph display of a subject such as a human body according to a distribution of radiation absorption coefficients. More specifically, the apparatus projects a number of X-ray beams through the subject in various directions, detects how much each X-ray beam is absorbed by the subject thereby to obtain a distribution of the X-ray absorption coefficients, and reconstructs a distribution of the X-ray absorption coefficients in a single plane of the subject, whereby the plane is photographed.

Computed tomography apparatus are classified into "first generation", "second generation" and "third generation", according to the method they employ to apply X-ray beams to the subject. The computed tomography apparatus is provided with an X-ray source and a detector or detectors, no matter which generation it belongs to.

Figure 1:
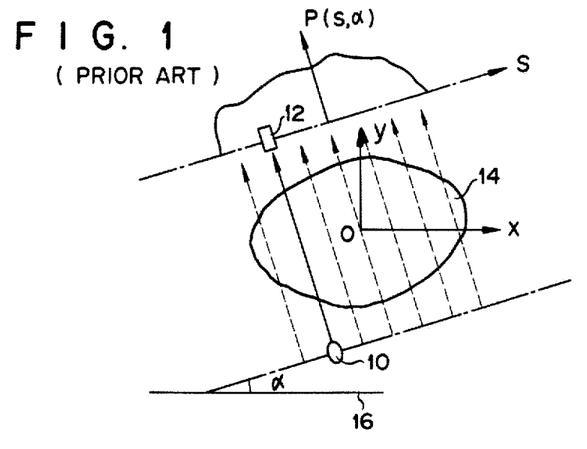
FIG. 1 is a diagram showing how a known apparatus obtains X-ray absorption data.

Now referring to FIG. 1, it will be described how X-ray beams are applied in a known computed tomography apparatus of the first generation. As shown in FIG. 1, an X-ray source 10 and a detector 12 are placed opposite each other with a subject 14 placed between them. The source 10 and the detector 12 are moved at the same speed in parallel linear directions. While moving this way, the source 10 scans the subject 14 with many X-ray beams and the detector 12 receives many X-ray beams coming directly from the source 10 or indirectly through the subject 14. During each round of scanning, the X-ray source 10 emits several hundred X-ray beams which are parallel to one another and spaced at regular intervals. After a first round of scanning, the X-ray source 10 and the detector 12 are again moved in parallel linear directions which are inclined at a small angle, thereby carrying out a second round of scanning. After the second round of scanning, the source 10 and the detector 12 are moved in parallel linear directions which are inclined at a small angle, thus achieving a third round of scanning. The scanning is repeated in this manner until the X-ray source 10 and the detector 12 orbit once around the subject 14. As a result, the detector 12 provides a number of sets of X-ray absorption data, each set obtained by one round of scanning.

Using the X-ray absorption data thus provided, a distribution of X-ray absorption coefficients in a single plane of the subject 14 is reconstructed. Practically, use is not made of the direct data values which have been obtained by the detector 12 and which represent how much each X-ray beam has been absorbed by the subject 14. Rather, the logarithmic values of these data are utilized.

Here, symbol P (s, $\alpha$) is used to denote the logarithmic data (hereinafter called "parallel beam projection data") which corresponds to the set of data values obtained by one round of scanning. "s" is the distance for which the X-ray source 10 and the detector 12 are moved, and "$\alpha$" is the angle at which the travel directions of the source 10 and the detector 12 are inclined to a reference axis 16.

A coordinate system, whose X axis is parallel to the reference axis 16 and whose origin is the point around which the X-ray source 10 and the detector 12 orbit, is used in order to reconstruct a distribution of X-ray absorption coefficients. Let f(x, y) denote the original distribution of X-ray absorption coefficients. Then, f(x, y) can be expressed as follows by the formula of Radon:

$$f(x, y) = \frac{-1}{(2\pi)^2} \int_0^{2\pi} Pf \int_{-\infty}^{\infty} \frac{P(s, \alpha)}{[s - (x\cos\alpha + y\sin\alpha)]^2} \, ds \, d\alpha \quad (1)$$

$$Pf \int_{-\infty}^{\infty}$$

in equation (1) is a singular integral and is defined as follows with respect to a smooth function b(s):

$$Pf \int_{-\infty}^{\infty} \frac{b(s)}{s^2} \, ds = \int_0^{\infty} \frac{b(s) + b(-s) - 2b(0)}{s^2} \, ds \quad (2)$$

Several methods to solve equation (1) are provided in view of the fact that the parallel beam projection data P(s, $\alpha$) is obtained only discretely in practice, and noise inevitably enters into the data P(s, $\alpha$) during each round of scanning. For example, the original distribution f(x, y) may be reconstructed by the convolution method. Suppose the projection data P(s, $\alpha$) is sampled at a point ($s_i$, $\alpha_j$) which is defined by one of a set of points spaced at regular intervals $\Delta s$ in the travel direction of the X-ray source 10 which inclines at an angle to the reference axis 16 and that the travel direction of the X-ray source 10 and the detector 12 is inclined at an angle of $\Delta \alpha$ before every round of scanning. If a point, at which the original distribution of X-ray absorption coefficients is reconstructed, is denoted by ($x_m$, $y_n$) and the convolution function is denoted by h(s), the original distribution f($x_m$, $y_n$) is represented as follows:

$$\overline{f(x_m, y_n)} = \sum_j (\overline{P}(x_m\cos\alpha_j + y_n\sin\alpha_j, \alpha_j)) \Delta\alpha \quad (3)$$

where:

$$\overline{P}(s_i, \alpha_j) = \sum_{i'} (h(s_i - s_{i'}) P(s_{i'})) \Delta s \quad (4)$$

To reconstruct the original distribution of X-ray absorption coefficients, other methods such as the iterative method, the Fourier transformation method and the filtered back projection method may be used. In any of these methods the original distribution is reconstructed, using the parallel beam projection data P(s, $\alpha$).

In computed tomography apparatus of the first generation the travel directions of the X-ray source 10 and the detector 12 can be inclined but at an extremely small angle before each round of scanning is carried out. Otherwise, a clear-cut image could not be obtained. In consequence, X-ray beams must be applied to the subject 14 for a long time to obtain X-ray absorption data sufficient to obtain a clear-cut image. It is very difficult to hold the subject motionless for such a long time, particulary when the subject is a human being. If the subject moves during the X-ray beam scanning, a phenomenon called "artifact" will occur.

To shorten the X-ray beam scanning time, second generation computed tomography apparatus has been provided with an X-ray source which supplies a narrow fan beam having an angle of diversion of 2°–3° and a linear array of detectors the number of which depends on the angle of diversion of the fan beam. The X-ray source and the array of detectors are moved in the same way as in the apparatus of the first generation. If the angle of diversion is $\gamma°$, the apparatus can obtain $\gamma$ times as many parallel beam projection data as does the apparatus of the first generation with $\Delta\alpha=1°$, upon completion of a single round of scanning. As a result, the X-ray scanning time becomes $\gamma$ times shorter than that required by the apparatus of the first generation in order to sample out data from the same number of sampling points.

The computed tomography apparatus of the third generation is provided with an X-ray source which emits a fan beam having an angle of diversion of 30°–40° and thus covering the entire subject and an arcuate array of detectors which can receive the whole fan beam. The X-ray source and the array of detectors are placed opposite each other with a subject placed between them. They are rotated around the subject, maintaining their relative positions. While rotating in this way, the X-ray source applies the fan beam to the subject and the detectors receive the fan beam coming through the subject, whereby the detectors obtains X-ray absorption data. Since the X-ray source and the detectors need not be moved linearly many times, the X-ray scanning time is far shorter than that required in the computed tomography apparatus of the first or second generation.

The data obtained by the computed tomography apparatus of the third generation are not parallel beam projection data. That is, they have not been obtained by scanning the subject with parallel X-ray beams which are spaced at regular intervals from one another. These data are called "fan beam projection data." If fan beam projection data are used, the original distribution of X-ray absorption coefficients cannot be reconstructed directly based on equations (3) and (4). It is therefore necessary to reorder the fan beam projection data into parallel beam projection data in order to reconstruct the original distribution f(x, y) according to equations (3) and (4). In practice, such reordering of data is achieved by interpolation since the fan beam projection data are discrete or discontinuous. An image representing a distribution of X-ray absorption coefficients constructed by such reordering of data is not clear or does not have a uniform granularity. A clear-cut image may be obtained if fan beam projection data are reordered to parallel beam projection data by means of interpolation of a high order. However, the interpolation of a high order is so complicated a step that it takes a considerably long time to accomplish the reordering of data. Moreover, the reordering of data cannot be conducted simultaneously with the collection of fan beam projection data. In other words, the reordering of data cannot be started until all the fan beam projection data are obtained. Thus the computed tomography apparatus of the third generation cannot provide an image until all the fan beam projection data are collected, unlike the apparatus of the first and second generations which can construct an image simultaneously with the collection of parallel beam projection data.

Although it can obtain an image substantially upon completion of data collection, the computed tomography apparatus of the first or second generation requires a relatively long time to collect the data. By contrast, although it can collect data in a relatively short time, the computed tomography apparatus of the third generation requires a considerably long time to reconstruct an image.

An object of this invention is to provide an apparatus for controlling a tomograph display using a fan beam, which uses radiation absorption data obtained by applying a fan beam to a subject to reconstruct in a short time a distribution image of radiation absorption coefficients of the subject, without converting the radiation absorption data into such radiation absorption data as would be obtained if parallel radiation beams were applied to the subject.

The invention is embodied by an apparatus comprising a scanner means which moves around a subject in an orbit existing on a specific plane, which scans the subject at predetermined sample times while moving once around the subject and which includes a radiation source for emitting a fan beam and a detector unit for receiving a fan beam and producing detection signals representing the absorption amount of the fan beam; means for producing modified signals by processing the detection signals with filtering function signals; means for obtaining data from said modified signals which is back-projected onto a reference line existing on the specific plane according to the distance between the radiation source and the reference line; and means for obtaining, according to the distance between the radiation source and the reference line and the distance between the reference line and a given point of the subject existing on the specific plane, data representing how much each detection signal contributes to the radiation absorption coefficient for a selected point and for adding up the data thus obtained so as to obtain the radiation absorption coefficient for said selected point.

This invention can be more fully understood from the following detailed description when taken in conjunction with the accompanying drawings, in which.

Figure 2:
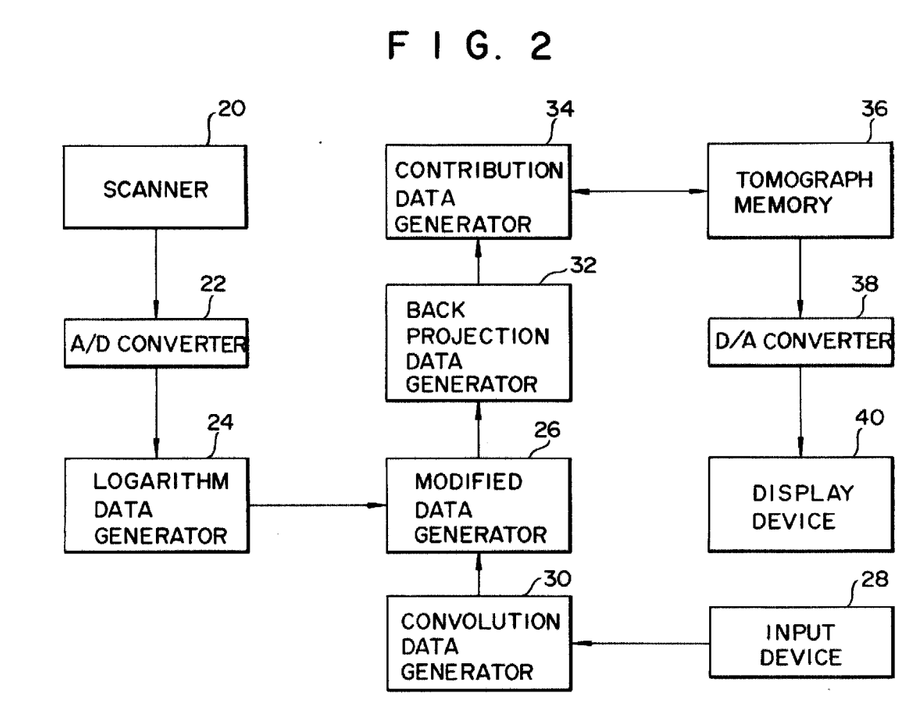
FIG. 2 is a general block circuit diagram illustrating an embodiment of this invention.

As schematically shown in FIG. 2, an apparatus for controlling a tomograph display using a fan beam according to this invention comprises a scanner 20, an A/D converter 22 and a logarithm data generator 24. The scanner 20 produces an electric signal which represents how much an X-ray beam has been absorbed by a subject. The signal is supplied to the A/D converter 22 and then to the logarithm data generator 24. The output signal of the logarithm data generator 24 is supplied to a modified data generator 26. To the modified data generator 26 there is connected a convolution data generator 30 which is selected to supply a desired convolution function by a signal supplied from an input device 28. The output data generated by the modified data generator 26 is supplied to a back projection data generator 32, the output data of which is supplied to a contribution data generator 34. The contribution data generator 34 is connected to a tomograph memory 36. The contents of the memory 36 are transferred via a D/A converter 38 to a display device 40 which produces a tomograph image based on the data stored in memory 36.

The construction and operation of the scanner 20 and the generators 26, 30, 32 and 34 is hereinafter described in detail.

Figure 3:
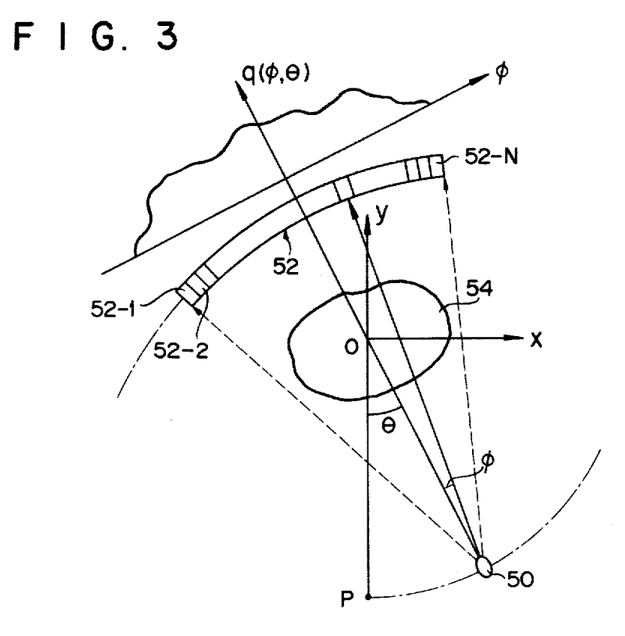
FIG. 3 is a diagram showing the positional relationship between a subject on one hand and an X-ray source and a detector on the other hand, which represent the scanner used in the embodiment shown in FIG. 2.

As shown in FIG. 3, the scanner 20 has an X-ray source 50 and a detector unit 52. The X-ray source 50 and the detector unit 52 lie directly opposite each other, and a subject 54 is placed between them. The detector unit 52 has a plurality of detectors 52-1, 52-2, ... 52-N which are juxtaposed to form an arcuate array. The X-ray source 50 emits a fan beam which has an angle of diversion of approximately 30° to 40° and which fully covers the entire subject 54. The X-ray source 50 and the detector unit 52 are secured to a rotatable member (not shown). The subject 54 is placed at such a position that its center coincides with the center of rotation of the rotatable member. The X-ray source 50 and the detector unit 52 are moved around the subject 54 in an orbit, while maintaining their positions relative to each other unchanged. Every time the rotatable member rotates by a predetermined angle, for example 1°, each of the detectors 52-1, 52-2, ... 52-N produces a detection signal which represents the ratio of the amount of X-rays it has received to the amount of X-rays emitted from the X-ray source 50.

The detection data produced by the detectors 52-1, 52-2, ... 52-N are converted into digital data by the A/D converter 22 (FIG. 2). The digital data are converted into logarithm data by the logarithm data generator 24, and the logarithm data thus obtained are supplied to the modified data generator 26. This data is called "fan beam projection data," each value of which is denoted here by the expression $q(\phi, \theta)$, where $\theta$ is the angle defined by a reference line OP connecting the center of rotation O and a reference position P of the X-ray source 50 and a line connecting the center O and the X-ray source 50, and $\phi$ is an angle defined by a line connecting the (N/2)th detector and the X-ray source 50 and a line connecting the X-ray source 50 and the detector which has produced the particular fan beam projection data value.

Let such a coordinate for indicating the original distribution $f(x, y)$ of X-ray absorption coefficients as shown in FIG. 3 be imagined, whose origin coincides with the center of rotation and whose Y axis coincides with said reference line OP, and let "S" denote the distance between the origin of the coordinate and the X-ray source 50. Then, the fan beam projection data $q(\phi, \theta)$ and the corresponding parallel beam projection data $P(s, \alpha)$ have the following relationship:

$$\left. \begin{array}{l} s = S \sin \phi \\ \alpha = \theta - \phi \end{array} \right\} \tag{5}$$

$$\frac{\partial(s, \alpha)}{\partial(\theta, \phi)} = S \cos \phi \tag{6}$$

therefore, $$q(\phi, \theta) = P(S \sin \phi, \theta - \phi) \tag{7}$$

Equation (6) is a Jacobian of the transformation of variables S and $\alpha$ into variables $\theta$ and $\phi$. If $P(S, \alpha) = 0$ for $S < |s|$, the original distribution $f(x, y)$ may be expressed as follows, by substituting equations (5), (6) and (7) for the corresponding terms of equation (1):

$$f(x, y) = \frac{-1}{(2\pi)^2} \int_0^{2\pi} \frac{S}{r(x, y, \theta)^2} Pf \int_{-\pi/2}^{\pi/2} \frac{q(\phi, \theta) \cos \phi}{\sin^2(\psi(x, y, \theta) - \phi)} d\phi d\theta \tag{8}$$

In equation (8), $$Pf \int_{-\pi/2}^{\pi/2}$$

denotes a singular integral and is defined as follows with respect to a smooth function $b(\phi)$:

$$Pf \int_{-\pi/2}^{\pi/2} \frac{b(\phi)}{\sin^2 \phi} d\phi = \int_0^{\pi/2} \frac{b(\phi) + b(-\phi) - 2b(0)}{\sin^2 \phi} d\phi \tag{9}$$

Figure 4:
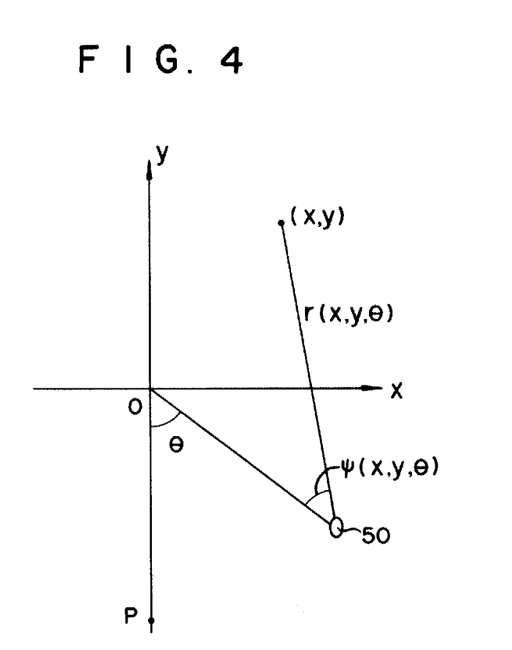
FIG. 4 shows a coordinate system which illustrates how to obtain the original distribution f(x, y) in the embodiment shown in FIG. 2.

As illustrated in FIG. 4, $r(x, y, \theta)$ is the distance between the X-ray source 50 and a pixel $(x, y)$ whose original distribution of X-ray absorption coefficients is to be reconstructed, and $\psi(x, y, \theta)$ is the angle defined by a line connecting the origin O and the X-ray source 50 and a line connecting the pixel $(x, y)$ and the X-ray source 50. They are represented as follows:

$$\left. \begin{array}{l} r(x, y, \theta) = \sqrt{(x - S\sin\theta)^2 + (y + S\cos\theta)^2} \\ \psi(x, y, \theta) = \theta + \tan^{-1}\left(\frac{x - S\sin\theta}{y + S\cos\theta}\right) \end{array} \right\} \tag{10}$$

As equation (10) suggests, the apparatus according to this invention reconstructs the original distribution $f(x, y)$ based on equation (8), using fan beam projection data $q(\phi, \theta)$. The original distribution $f(x, y)$ is reconstructed in two separate steps which are expressed as follows:

$$\tilde{q}(\phi, \theta) = \frac{-1}{2\pi^2} Pf \int_{-\pi/2}^{\pi/2} \frac{q(\phi', \theta) \cos \phi'}{\sin^2(\phi - \phi')} d\phi' \tag{11}$$

$$f(x, y) = \frac{1}{2} \int_O^{2\pi} \frac{S}{r(x, y, \theta)^2} \bar{q}(\psi(x,y,\theta), \theta) d\theta. \quad (12)$$

$\bar{q}(\phi, \theta)$ is called "modified data". Since the Fourier series expansion of the smooth function $b(\phi)$ which is defined as $-\pi/2 \leq \phi < \pi/2$ is represented by the following equations (13), equation (11) may be expressed as the following equations (14):

$$\left.\begin{array}{l} b_n = F_\phi(b(\phi)) = \frac{1}{\pi} \int_{-\pi/2}^{\pi/2} b(\phi) e^{2ni\phi} d\phi \\ b(\phi) = F_\phi^{-1}(b_n) = \sum_n b_n e^{-2ni\phi} \end{array}\right\} \quad (13)$$

$$\left.\begin{array}{l} q_n(\theta) = F_\phi(q(\phi, \theta) \cos \phi) \\ \bar{q}(\phi, \theta) = \pi F_\phi^{-1}\left(\frac{|n|}{\pi^2} q_n(\theta)\right) \end{array}\right\} \quad (14)$$

$F_\phi^{-1}$ denotes the Fourier series expansion.

The fan beam projection data $q(\phi, \theta)$ supplied to the modified data generator 26 contain a noise component of high harmonic waves. The modified data $\bar{q}(\phi, \theta)$ is therefore supplied to a lowpass filter (not shown) which has a filtering function $H_n$, where n denotes the order of the high harmonic waves. Then, the modified data $\bar{q}(\phi, \theta)$ is expressed as follows:

$$\bar{q}(\phi, \theta) = \pi \cdot F_\phi^{-1}\left(\frac{|n|}{\pi^2} H_n q_n(\theta)\right) \quad (15)$$

Further, the modified data $\bar{q}(\phi, \theta)$ can be expressed as follows if the nature of the Fourier series and the convolution function data $h(\phi)$ are taken into consideration:

$$h(\phi) = F_\phi^{-1}\left(\frac{|n|}{\pi^2} H_n\right) \quad (16)$$

$$\bar{q}(\phi, \theta) = h(\phi) * (q(\phi, \theta) \cos \phi) \quad (17)$$

Symbol * indicates convolution with respect to the angle $\phi$.

Figure 5:
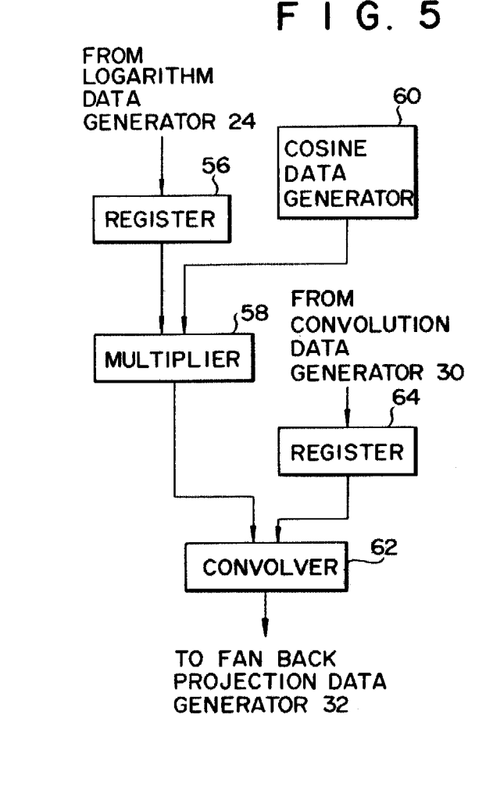
FIG. 5 is a block circuit diagram showing a modified data generator which may be utilized in the embodiment of FIG. 2.

That is, modified data $\bar{q}(\phi, \theta)$ are obtained according to equation (17) by the modified data generator 26. As shown in FIG. 5, the modified data generator 26 comprises a register 56, a multiplier 58, a cosine data generator 60, a convolver 62 and another register 64. The register 56 receives a value of the fan beam projection data $q(\phi, \theta)$ from the logarithm data generator 24 and supplies it to one input terminal of a multiplier 58. The cosine data generator 60 generates a signal representative of $\cos\phi$, "$\phi$" being the position of the individual detector 52-1, 52-2, . . . or 52-N producing the data value in register 56. Generator 60 has its output terminal connected to the other input terminal of the multiplier 58. The multiplier 58 multiplies fan beam projection data value $q(\phi, \theta)$ by cosine data $\cos\phi$, and its output data, i.e. $q(\phi, \theta) \cos\phi$, is supplied to one input terminal of the convolver 62. The convolver 62 convolves $q(\phi, \theta) \cos\phi$ and a convolution function value $h(\phi)$ supplied from the convolution data generator 30 through the register 64. The result of the convolution, i.e. $h(\phi)*q(\phi, \theta)\cos\phi$, is supplied to the back projection data generator 32.

If the fan beam projection data values $q(\phi, \theta)$ are sampled with respect to the angle $\phi$ at sampling intervals of $\Delta\phi$ and are sampled with respect to the angle $\theta$ at sampling intervals of $\Delta\theta$, the convolver 62 carries out an arithmetic operation expressed by the following equation which is a discrete form of equation (17):

$$\bar{q}(\phi_i, \theta_j) = \sum_i (h(\phi_i - \phi_i') q(\phi_i', \theta_j) \cos\phi_i')\Delta\phi \quad (18)$$

Obviously, the convolution function data $h(\phi)$ largely influences the quality of the image to be obtained. It is therefore desired that $h(\phi)$ be readily changeable if necessary. With this invention it is possible to produce a convolution function data $h(\phi)$ according to equation (16) only if the input device 28 (FIG. 2) selects a proper filtering function $H_n$. The filtering function $H_n$ can be expressed by a simple formula of n in most cases. And the operator can easily change one function $H_n$ to another, while viewing the displayed image.

Figure 6:
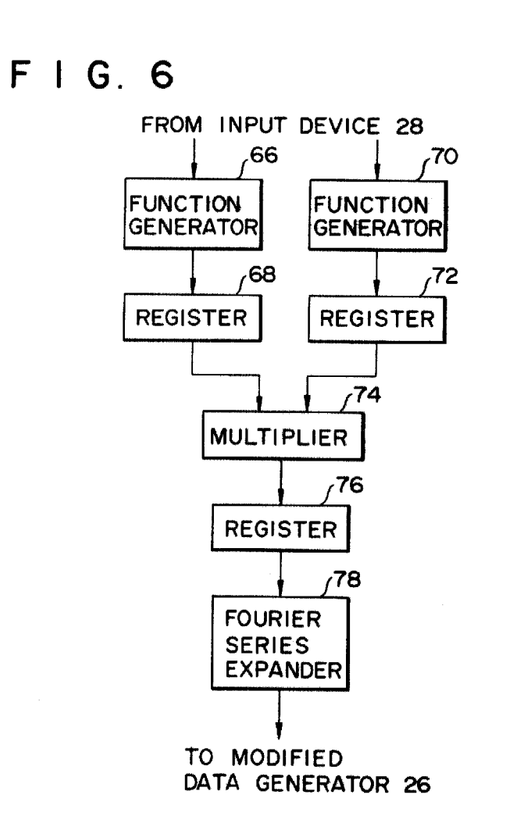
FIG. 6 is a block diagram showing a convolution data generator which may be used in the embodiment of FIG. 2.

The convolution data generator 30 has such a structure as shown in FIG. 6. When the operator operates the input device 28, thereby selecting a desired function $H_n$, a first function generator 66 generates filtering function data values $H_n$ and at the same time a second function generator 70 generates data values $|n|/\pi^2$. Values for $H_n$ and $|n|/\pi^2$ are supplied to the registers 68 and 72, respectively. The registers 68 and 72 are connected to two input terminals of a multiplier 74, respectively. Upon receipt of the data from the registers 68 and 72 the multiplier 74 produces an output data representing $|n|/\pi^2 H_n$, which is supplied to a register 76. The register 76 is connected to a Fourier series expander 78. The expander 78 carries out Fourier series expansion of the contents of the register 76, thereby obtaining convolution function data values $h(\phi)$ in accordance with equation (16). Each convolution function data value $h(\phi)$ thus obtained is supplied to the modified data generator 26.

Using the modified data $\bar{q}(\phi, \theta)$ and $r(x, y, \theta)$ and $\psi(x, y, \theta)$ which are expressed by equations (10), the original distribution $f(x, y)$ may be computed with respect to each pixel by accumulating values determined in accordance with equation (12). But this method of computation requires a long time. According to this invention, the fan beam projection data are back-projected onto only the pixels which exist on a selected reference line.

Figure 7:
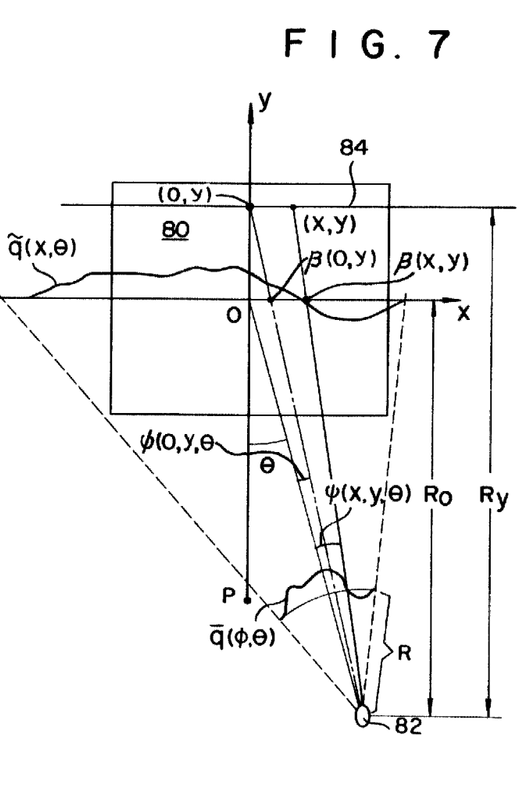
FIG. 7 is a coordinate system diagram explaining how the embodiment of FIG. 2 carries out back projection.

FIG. 7 is a coordinate system explaining how the back projection is carried out. In the coordinate system there is an imaginary two-dimensional matrix 80 on which the original distribution $f(x, y)$ is reconstructed. The origin O of the coordinate system coincides with the center of an orbit in which an X-ray source 82 moves. The distance S between the origin and the X-ray source 82 therefore remains unchanged. The Y axis of the coordinate system coincides with the afore-defined reference line OP. Suppose modified data values $\bar{q}(\phi, \theta)$ are obtained from fan beam projection data values $q(\phi, \theta)$ which are produced when the reference line OP and a line connecting the origin and the X-ray source 50 define an angle $\theta$ and that the modified data $\bar{q}(\phi, \theta)$ are distributed on an arc the center of which coincides with the X-ray source 50 and which has a predetermined radius R (for example R = 1). Then, if the modified data $\bar{q}(\phi, \theta)$ is back-projected exclusively onto a reference line in the matrix 80, for example the X axis of the coordinate system, there will be obtained back projection data $\tilde{q}(x, \theta)$ for the pixels on the X axis, which data are expressed as follows:

$$\tilde{q}(x, \theta) = \frac{\bar{q}(\psi(x, o, \theta), \theta)}{r(x, o, \theta)^2} \tag{19}$$

$\psi(x, o, \theta)$ and $r(x, o, \theta)$ are obtained according to equations (10). The calculation is actually carried out in a discrete form. Suppose the back projection data $\tilde{q}(x, \theta)$ are sampled with respect to the X axis at sampling (pixel) intervals of $\Delta x_j$, the equation (19) is expressed as follows:

$$\tilde{q}(x_k, \theta_j) = \frac{\bar{q}(\psi(x_k, o, \theta_j), \theta_j)}{r(x_k, o, \theta_j)^2} \tag{20}$$

The modified data $\bar{q}(\phi, \theta)$ are also sampled at the sampling point $(\phi_i, \theta_j)$. Therefore, $\bar{q}(\psi(x_k, o, \theta_j), \theta_j)$ is obtained by interpolating the modified data $\bar{q}(\phi_i, \theta_j)$. It is desirable that the sampling interval $\Delta x_j$ be varied according to the angle $\theta_j$. It is necessary to determine how much the modified data $\bar{q}(\phi, \theta)$ contribute to the distribution to be reconstructed at any given pixel (x, y) of the two-dimensional matrix 80. This is achieved by distributing the back projection data $\tilde{q}(x, \theta)$ to pixels in accordance with the distances between the pixel and the sampling points on the reference line. If the X axis of the coordinate system is used as the reference line of the two-dimensional matrix 80, the contributions $\Delta_\theta f(x, y)$ of the data $\tilde{q}(x, \theta)$ to the pixels will be expressed as follows:

$$\Delta_\theta f(x, y) = C \tilde{q}(\beta(x, y), \theta) \frac{Ro^2}{Ry^2} \tag{21}$$

In equation (21), C denotes a constant, Ro the length of a line connecting the X-ray source 50 and the X axis of the coordinate system and extending perpendicular to X axis, Ry denotes the length of a line connecting the X-ray source 50 and a line 84 parallel to X axis through the pixel (x, y) under consideration and extending perpendicular to the line 84, and $\beta(x, y)$ a point where the line connecting the X-ray source 50 and the pixel (x, y) intersects the X axis of the coordinate system. That is:

$$\left. \begin{array}{l} Ro = S \cos\theta \\ Ry = y + S \cos\theta \\ \beta(x, y) = \beta(o, y) + \frac{Ro}{Ry} x \end{array} \right\} \tag{22}$$

In equation (22), $\beta(o, y)$ denotes a point where the line connecting the X-ray source 50 and the point (o, y) intersects the X axis and is expressed as follows:

$$\beta(o, y) = S \sin\theta - Ro \tan(\theta - \psi(o, y, \theta)) \tag{23}$$

The data $\beta(x, y)$ are linear with respect to "x", and $Ro^2/Ry^2$ does not depend on "x".

That is, to reconstruct the original distribution f(x, y) with respect to the pixel (x, y), it is sufficient to add up, as expressed as follows, the contributions $\Delta_\theta f(x, y)$ of the fan beam projection data $q(\phi, \theta_j)$ obtained from X-ray beams of the $\theta_j$ direction, which have been obtained by applying X-rays in various directions onto the subject 54:

$$f(x, y) = \sum_j (\Delta_{\theta_j} f(x, y)) \Delta\theta \tag{24}$$

Preferably, the X axis is used as the reference line when $\theta \in J_1 = [o, \frac{1}{4}\pi) \cup [\frac{3}{4}\pi, 5/4\pi) \cup [7/4\pi, 2\pi)$, and the Y axis is used as the reference line when $\theta \in J_2 = [\frac{1}{4}\pi, \frac{3}{4}\pi) \cup [5/4\pi, 7/4\pi)$, where "U" denotes a logical sum, "(A, . . . " denotes a boundary value including "A", and ". . . , A)" denotes a boundary value not including "A." If the Y axis of the coordinate system is used as the reference line of the two-dimensional matrix 80, the following data q(y, $\theta$) will be obtained by back-projecting the modified data $\bar{q}(\phi, \theta)$ onto a point y on Y axis:

$$\tilde{q}(y, \theta) = \frac{\bar{q}(\psi(o, y, \theta), \theta)}{r(o, y, \theta)^2} \tag{25}$$

The calculation is also carried out in a discrete form in practice. Suppose the back projection data $\tilde{q}(y, \theta)$ are sampled with respect to the Y axis at sampling intervals of $\Delta y_j$, the equation (25) is expressed as follows:

$$\tilde{q}(y_k, \theta_j) = \frac{\bar{q}(\psi(o, y_k, \theta_j), \theta_j)}{r(o, y_k, \theta_j)^2} \tag{26}$$

The modified data $\bar{q}(\phi, \theta)$ are also sampled at the sampling point $(\phi_i, \theta_j)$. As before, $\bar{q}(\psi(o, y_k, \theta_j), \theta_j)$ is obtained by interpolating the modified data $\bar{q}(\phi_i, \theta_j)$. It is desirable that the sampling interval $\Delta y_j$ is varied according to the angle $\theta_j$.

In this case, the contributions $\Delta_\theta f(x, y)$ of the modified data $\bar{q}(y, \theta)$ will be expressed as follows:

$$\Delta_\theta f(x, y) = C \tilde{q}(\beta'(x, y), \theta) \frac{Ro^2}{Rx^2} \tag{27}$$

In equation (27), Ro denotes the length of a line connecting the X-ray source 50 and the Y axis and extending perpendicular to the Y axis, Rx the length of a line connecting the X-ray source 50 and a line parallel to the Y axis through the pixel (x, y) and extending perpendicular to the line, and $\beta'(x, y)$ denotes the point where the line connecting the X-ray source 50 and the pixel (x, y) intersects the Y axis. That is:

$$\left. \begin{array}{l} Ro = S \sin\theta \\ Rx = -x + S \sin\theta \\ \beta'(x, y) = \beta'(x, o) + \frac{Ro}{Rx} y \end{array} \right\} \tag{28}$$

In equation (28), $\beta'(x, o)$ denotes a point where the line connecting the X-ray source 50 and the point (x, o) intersects with the Y axis and is expressed as follows:

$$\beta'(x, o) = -S \cos\theta + Ro \cot(\theta - \psi(x, o, \theta)) \tag{29}$$

Equations (25) and (27) are identical with equations (19) and (21), respectively. Also the data $\beta'(x, y)$ are linear with respect to "y", and $Ro^2/Rx^2$ does not depend on "y".

Figure 8:
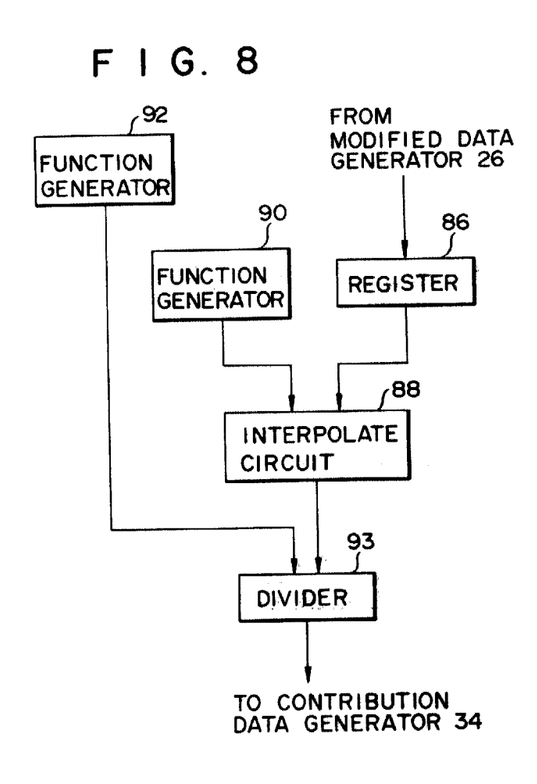
FIG. 8 is a block diagram showing a back projection data generator which may be used in the embodiment of FIG. 2.

The back projection data generator 32 is constructed as illustrated in FIG. 8. The values of modified data $\bar{q}(\phi, \theta)$ from the modified data generator 26 are supplied to a register 86, which is connected to an interpolate circuit 88. The back projection data generator 32 includes two function generators 90 and 92. The function generator 90 produces function data $\psi(x, o, \theta)$ or $\psi(o, y, \theta)$ according to equation (10) and supplies it to the interpolate circuit 88. The interpolate circuit 88 interpolates $\bar{q}(\psi(x, o, \theta), \theta)$ based on the modified data $\bar{q}(\phi, \theta)$. The output data of the interpolate circuit 88 is supplied to one input terminal of a divider 93. The function generator 92 produces function data $r(x, o, \theta)$ or $r(o, y, \theta)$ according to equation (10) and supplies it to the other input terminal of the divider 93. According to the value of $\theta$ the divider 93 carries out an arithmetic operation which is defined by equation (19) or equation (25). The output data, $\bar{q}(x, \theta)$ or $\bar{q}(y, \theta)$, of the divider 93 is then supplied to the contribution data generator 34.

Figure 9:
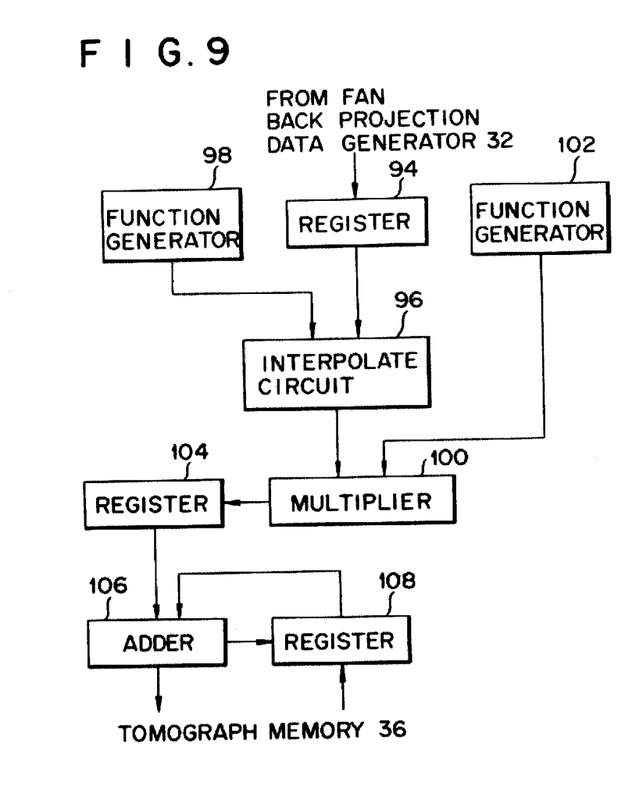
FIG. 9 is a block diagram showing a contribution data generator which may be used in the embodiment of FIG. 2.

The contribution data generator 34 is constructed as shown in FIG. 9. The output data of the divider 93, i.e. $\bar{q}(x, \theta)$ or $\bar{q}(y, \theta)$, is supplied to a register 94. The register 94 is connected to an interpolate circuit 96. A function generator 98 is connected also to the interpolate circuit 96. The generator 98 produces a function data value $\beta(x, y)$ or $\beta'(x, y)$ with respect to a pixel $(x, y)$, the original distribution $f(x, y)$ of which is to be obtained. The function data is supplied to the interpolate circuit 96. The interpolate circuit 96 interpolates $\bar{q}(\beta(x, y), \theta)$ based on $\bar{q}(x, \theta)$ or $\bar{q}(\beta'(x, y), \theta)$ based on $\bar{q}(y, \theta)$. The output data of the interpolate circuit 96 is supplied to one input terminal of a multiplier 100. The contribution data generator 34 is provided with another function generator 102 which produces a function data value $C(R_o^2/R_y^2)$ or $C(R_o^2/R_x^2)$ according to equation (22) or (28) and which supplies the function data to the other input terminal of the multiplier 100. According to the value of $\theta$ the multiplier 100 carries out an arithmetic operation which is defined by equation (21) or (27). The output data values of the multiplier 100, i.e. contribution data $\Delta_\theta f(x, y)$, are supplied to a register 104. The output data of the register 104 is supplied to one input terminal of an adder 106. The output terminal of the adder 106 is connected to a tomograph memory 36. The content of the tomograph memory 36 is supplied to a register 108, the output terminal of which is connected to the other input terminal of the adder 106. The adder 106 carries out an arithmetic operation according to equation (24). When the adder 106 adds up all the contributions $\Delta_\theta f(x, y)$ with respect to a pixel $(x, y)$, the original distribution $f(x, y)$ is generated in the tomograph memory 36. Upon receiving the original distribution $f(x, y)$ with respect to all the pixels $(x, y)$, the memory 36 supplies its contents via the D/A converter 38 to the display device 40 (FIG. 2). As a result, the display device 40 displays a reconstructed image of the original distribution of X-ray absorption coefficients of the subject 54.

Now referring to the flow charts given in FIGS. 10A to 10C, it will be described how the apparatus of FIG. 2 processes data, thereby producing the tomograph display.

Figure 10A:
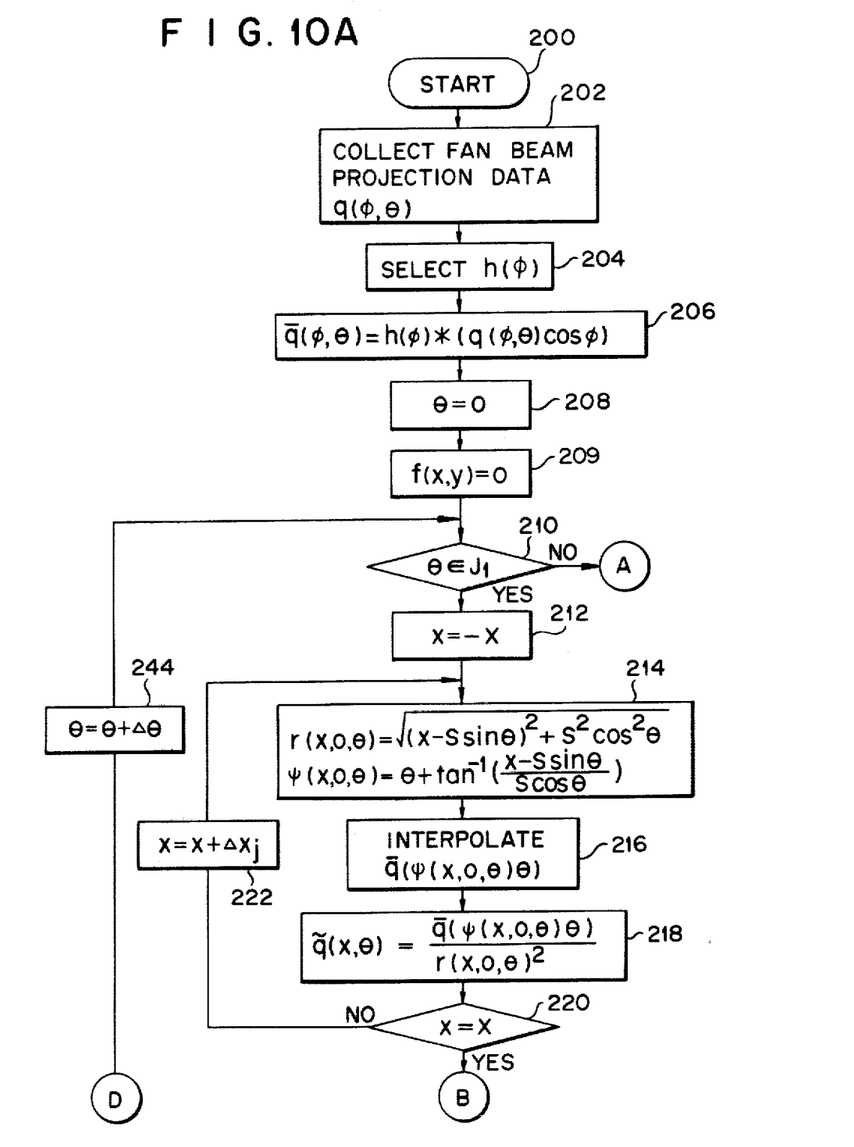
FIGS. 10A to 10C are flow charts illustrating how the embodiment of FIG. 2 operates.
Figure 10B:
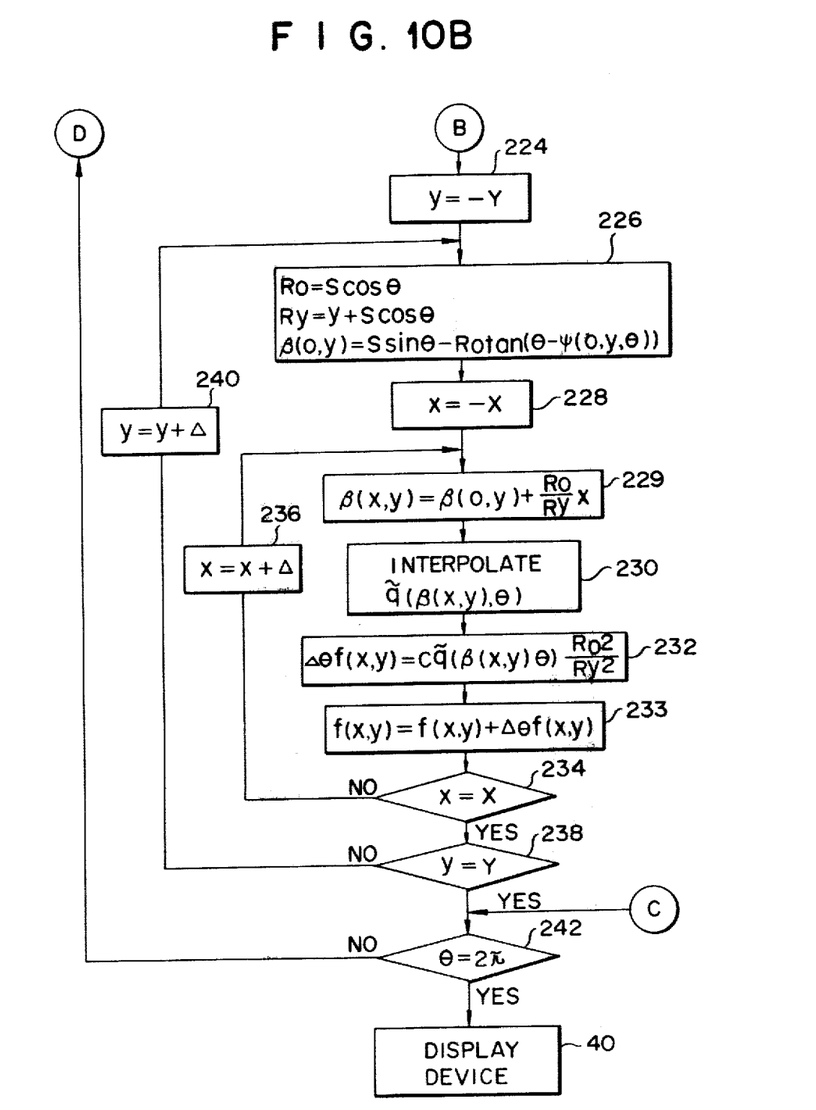
Figure 10C:
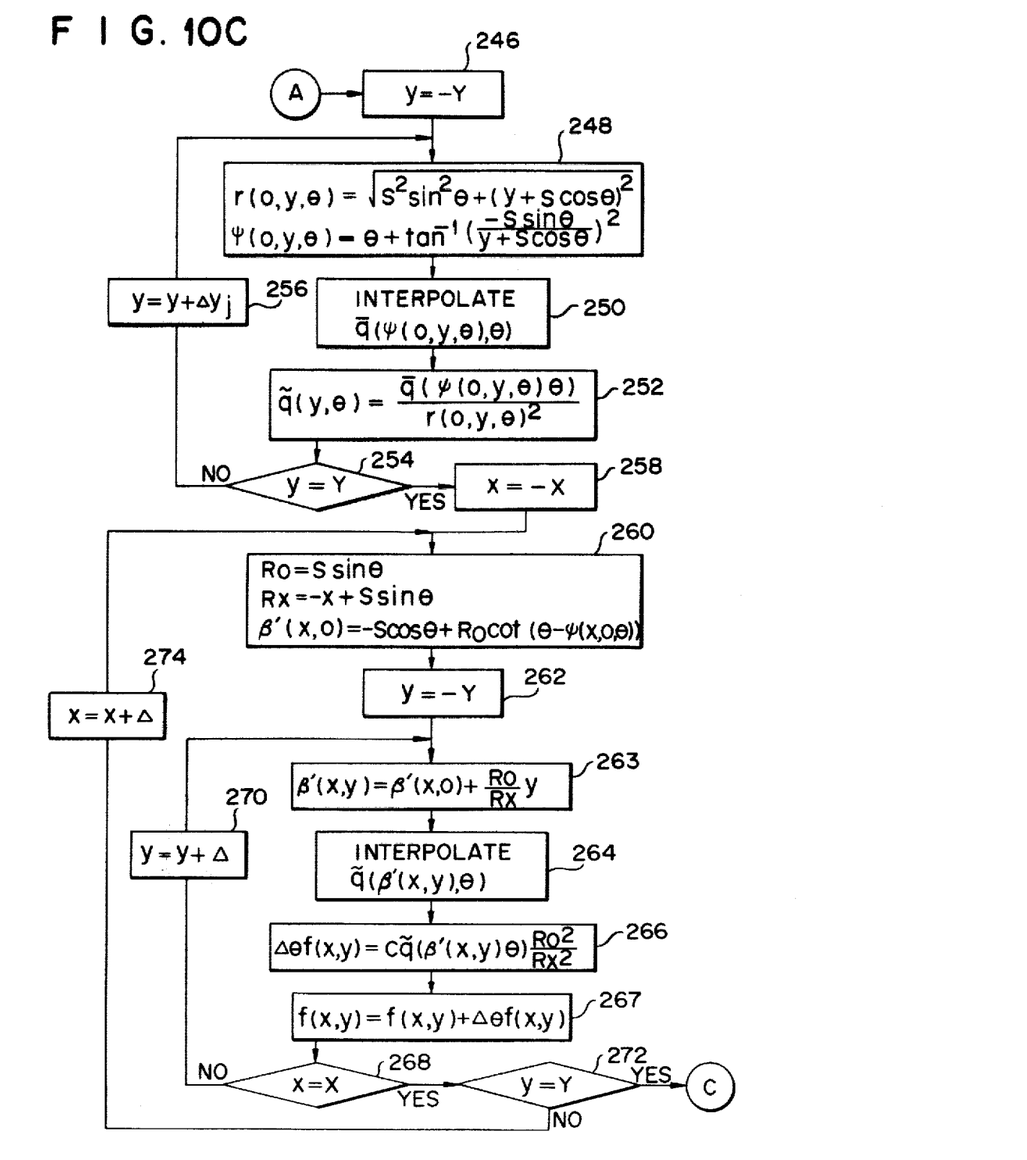

As shown in FIG. 10A, first in routine 200 the rotatable member (not shown) of the scanner 20 (FIG. 2) is rotated intermittently each time by $\Delta\theta$, the X-ray source 50 applies a fan beam onto the subject 54 (FIG. 3) every time the rotatable member turns by $\Delta\theta$, and the detector unit 52 receives the X-rays coming through the subject 54. In routine 202, fan beam projection data $q(\phi, \theta)$ are collected. Then, in routine 204 a convolution function data $h(\phi)$ is selected. In routine 206 the fan beam projection data $q(\phi, \theta)$ and the convolution function data $h(\phi)$ are convolved, thereby obtaining modified data $\bar{q}(\phi, \theta)$. Then, as described below, the modified data $\bar{q}(\phi, \theta)$ are back-projected with respect to only the X axis or Y axis, thus obtaining back projection data $\bar{q}(x, \theta)$ or $\bar{q}(y, \theta)$. In routine 208, $\theta$ is set to $0°$. In routine 209, $f(x, y)$ is set to 0. Then, in routine 210 it is judged if $\theta \in J_1 = [0, \frac{1}{4}\pi) \cup [\frac{3}{4}\pi, 5/4\pi) \cup [7/4\pi, 2\pi)$. If $\theta \in J_1$, x is set to $-X$ in routine 212 in order to back-project the modified data $\bar{q}(\phi, \theta)$ with respect to the X axis. Here let it be assumed that an X-Y coordinate system is used to indicate the original distribution of X-ray absorption coefficient and the original distribution is sampled with respect to the X axis and Y axis at intervals of $\Delta$, where x ranges from $-X$ to X and y ranges from $-Y$ to Y.

In routine 214, parameters $r(x, o, \theta)$ and parameter $\psi(x, o, \theta)$ are obtained in order to obtain back projection data $\bar{q}(x, \theta)$. In routine 216 data $\bar{q}(\psi(x, o, \theta), \theta)$ is obtained from the modified data $\bar{q}(\phi, \theta)$ by interpolation. In routine 218 back projection data $\bar{q}(x, \theta)$ are obtained from $\bar{q}(\psi(x, o, \theta), \theta)/r(x, o, \theta)^2$. In routine 220, x is compared with X. If x is not equal to X, $\Delta x_j$ is added to x in routine 222, whereby routine 214 is again executed.

When x is found to be equal to X in routine 220, the back projection data $\bar{q}(x, \theta)$ has been obtained for the pixels on the X axis by back-projecting onto the X axis the fan beam projection data $q(\phi, \theta)$ which are obtained by applying one fan beam onto the subject 54. Now that the back projection data $\bar{q}(x, \theta)$ has been obtained, contribution data $\Delta_\theta f(x, y)$ will be obtained in order to distribute the data $\bar{q}(x, \theta)$ to the individual pixels $(x, y)$. First, y is set to $-Y$ in routine 224, and parameters Ro, Ry and $\beta(o, y)$ are computed in routine 226. In routine 228, x is set to $-X$, and in routine 229 parameter $\beta(x, y)$ is computed. The back projection data $\bar{q}(\beta(x, y), \theta)$ are obtained from the back projection data $\bar{q}(x, \theta)$ by interpolating in routine 230. In routine 232, from $C \bar{q}(\beta(x, y), \theta) R_o^2/R_y^2$ there are obtained contribution data values $\Delta_\theta f(x, y)$ which represent how much the individual fan beam projection data $q(\psi, \theta)$ contribute to each pixel $(x, y)$. Here, C denotes a constant. $\Delta_\theta f(x, y)$ is added to $f(x, y)$ in routine 233. In routine 234, x is compared with X. If x is not equal to X, $\Delta$ is added to x in routine 236 and routine 229 will be executed again. If x is equal to X, y is compared with Y in routine 238. If y is not equal to Y, $\Delta$ is added to y in routine 240 and routine 226 will be executed again. If y is equal to Y, $\theta$ is compared with $2\pi$ in routine 242. If $\theta$ is not $2\pi$, $\Delta\theta$ is added to $\theta$ in routine 244 (FIG. 10A) and routine 210 will be executed again so as to judge if $\theta$ is in $J_1$.

If $\theta$ is found not to be in $J_1$ in routine 210, y is set to $-Y$ in routine 246 in order to back project the modified data $\bar{q}(\phi, \theta)$ onto the Y axis. The subsequent routines 246, 248, 250, 252, 254, 256 differ from the above-described routines 212, 214, 216, 218, 220 and 222 only in that y is processed instead of x. When y is found to be Y in routine 254, back projection data $\bar{q}(y, \theta)$ has been obtained for the pixels on the Y axis by back-projecting fan beam projection data $q(\phi, \theta)$ which are obtained by applying one fan beam onto the subject 54.

Then, the subsequent routines 258, 260, 262, 263, 264, 266, 267, 268, 270, 272 and 274 are executed, which differ from the above-described routines 224, 226, 228, 229, 230, 232, 233, 234, 236, 238 and 240 only in that different parameters are used. When y is found to be Y in routine 272, there is obtained contribution data $\Delta_\theta f(x,$ y) which represents how much the individual fan beam projection data values q(ψ, θ) contribute to each pixel (x, y).

When θ is found to be 2π in routine 242, the original distribution f(x, y) of X-ray absorption coefficients is obtained and then supplied to the display device 40. As a result, a tomograph is displayed by the display device 40.

With the above-described embodiment it is unnecessary to convert fan beam projection data into parallel beam projection data. The fan beam projection data can be processed in order to obtain a tomograph, thus providing a tomograph which is sufficiently clear. In addition, the embodiment can reduce the time necessary to reconstruct the original distribution of X-ray absorption coefficient.

Now another embodiment of this invention will be described. In this embodiment, modified data $\bar{q}(\phi, \theta)$ are obtained wihtout using a convolution function $h(\phi)$. That is, $q_n(\theta)$ and $\bar{q}(\phi, \theta)$ both defined by equations (14) are obtained in the following manner.

Suppose a function $b(\phi)$ defined by $-\pi/2 \leq \phi < \pi/2$ is set to 0 so long as $|\phi| > \pi/2$. The function $b(\phi)$ may be subjected to Fourier transformation in the following way:

$$B(\omega) = F(b(\phi)) = \int_{-\infty}^{\infty} b(\phi) e^{2\pi i \phi} d\phi,$$

where ω denotes frequency and F denotes that the function b(φ) undergoes Fourier transformation. Equations (14) are thus expressed as follows:

$$q_n(\theta) = F_\phi (q(\phi, \theta) \cos\phi) = \left[ \frac{1}{\pi} F(q(\phi, \theta) \cos\phi) \right] \left( \frac{n}{\pi} \right) \tag{30}$$

In equation (30) n denotes the order of high harmonic waves. Let $Q(\omega, \theta)$ denote $F(q(\phi, \theta) \cos\phi)$ here. Then, from equation (30), the following equation is obtained:

$$\frac{|n|}{\pi^2} q_n(\theta) = \left[ \frac{|\omega|}{\pi^2} Q(\omega, \theta) \right] \left( \frac{n}{\pi} \right) \tag{31}$$

If $q(\phi, \theta) \cos\phi$ is set to 0, where $-\pi/2 \leq \phi < -T$, $T < \phi < \pi/2$ and if a proper function $C(\omega)$ is used, the following equations will be practically established:

$$F^{-1}\left( \frac{|\omega|}{\pi^2} Q(\omega, \theta) + C(\omega) \right) (\phi) = 0 \\ -\frac{\pi}{2} \leq \phi < -T, \; T < \phi < \frac{\pi}{2} \tag{32}$$

In equations (32), $F^{-1}$ denotes Fourier inverse transformation. Equation (31) is subjected to Fourier series expansion in the following manner:

$$F_\phi^{-1}\left( \frac{|n|}{\pi^2} q_n(\theta) \right) = \tag{33}$$

-continued $$F_\phi^{-1}\left( \left( \frac{|\omega|}{\pi^2} Q(\omega, \theta) \left(\frac{n}{\pi}\right) + C\left(\frac{n}{\pi}\right) \right) \right) \\ - F_\phi^{-1}\left( C\left(\frac{n}{\pi}\right) \right)$$

Consequently, equations (14) are changed to the following:

$$\bar{q}(\phi, \theta) = \pi F_\phi^{-1}\left( \frac{|n|}{\pi^2} q_n(\theta) \right) \\ = \pi^2 F^{-1}\left( \frac{|\omega|}{\pi^2} Q(\omega, \theta) + C(\omega) \right) - \pi c(\phi) \\ c(\phi) = F_\phi^{-1}\left( C\left(\frac{n}{\pi}\right) \right) \tag{34}$$

In equations (34), $C(\omega)$ and $c(\phi)$ are predetermined functions, and $Q(\omega, \theta)$ is obtained by subjecting $q(\phi, \theta) \cos\phi$ to Fourier transformation. In practice, a lowpass filter having a filtering function $H(\omega)$ is used to remove noise component of high harmonic waves which is contained in fan beam projection data $q(\phi, \theta)$, whereby modified data $\bar{q}(\phi, \theta)$ are obtained in the following way:

$$\bar{q}(\phi, \theta) = \pi^2 F^{-1}\left( \frac{|\omega|}{\pi^2} H(\omega) Q(\omega, \theta) + C(\omega) \right) - \pi c(\phi) \tag{35}$$

Figure 11:
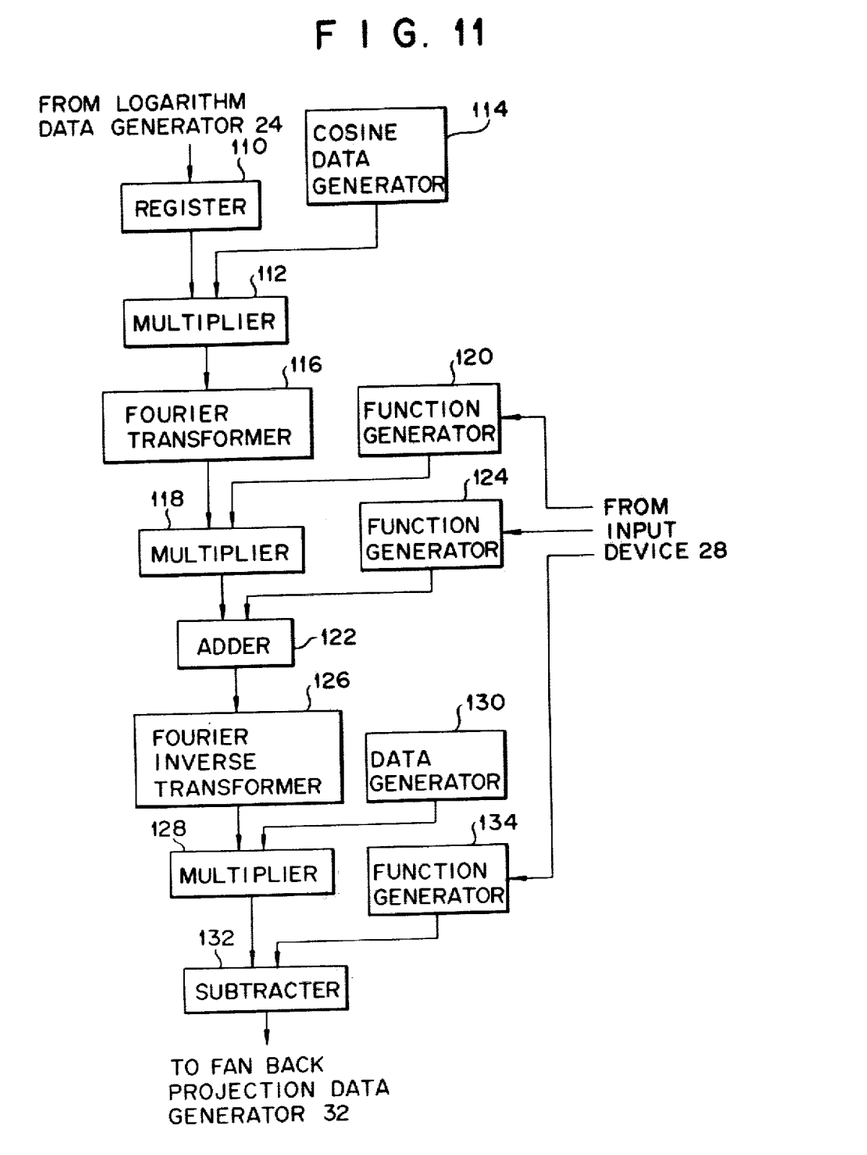
FIG. 11 is a block diagram showing a modified data generator according to a further embodiment of this invention.

The second embodiment is identical with the embodiment of FIG. 2, except that no convolution data generator is provided, that an input device 28 is connected directly to a modified data generator 26 and that the modified data generator 26 is constructed as illustrated in FIG. 11. As shown in FIG. 11, a register 110 receives fan beam projection data $q(\phi, \theta)$ from the logarithm data generator 24. The register 110 is connected to one input terminal of a multiplier 112. Connected to the other input terminal of the multiplier 112 is the output terminal of a cosine data generator 114 which produces cosine data $\cos\phi$, "φ" of which represent the positions of the detectors of a scanner 20. The multiplier 112 multiplies each fan beam projection data value $q(\phi, \theta)$ by each value of $\cos\theta$. The product of this multiplication, i.e. $q(\phi, \theta) \cos\phi$, is supplied to a Fourier transformer 116. The output data of the Fourier transformer, i.e. $F(q(\phi, \theta) \cos\phi) = Q(\omega, \theta)$, is supplied to one input terminal of another multiplier 118. To the other input terminal of the multiplier 118 there is connected a function generator 120 which generates a predetermined filtering function $|\omega|/\pi^2 H(\omega)$ designated by operating an input device 28. The output data, $|\omega|/\pi^2 H(\omega) Q(\omega, \theta)$, of the multiplier 118 is supplied to one input terminal of an adder 122. Connected to the other input terminal of the adder 122 is a function generator 124 which generates a predetermined function $C(\omega)$ designated by operating the input device 28. The output data of the adder 122, i.e. $|\omega|/\pi^2 H(\omega) Q(\omega, \theta) + C(\omega)$, is supplied to a Fourier inverse transformer 126. The output data of the Fourier inverse transformer 126, i.e. $F^{-1}(|\omega|/\pi^2 H(\omega) Q(\omega, \theta) + C(\omega))$, is supplied to one input terminal of a multiplier 128. Connected to the other input terminal of the multiplier 128 is a data generator 130 for generating a data value representing $\pi^2$. The output data of the multiplier, i.e. $\pi^2 F^{-1}(|\omega|/\pi^2 H(\omega) Q(\omega, \theta) + C(\omega))$, is supplied to one input terminal of a subtractor 132. To the other input terminal of the subtractor there is connected a function generator 134 which generates a function $\pi c(\phi)$ designated by operating the input device 28. Thus, the output data of the subtractor 132, i.e. $\pi^2 F^{-1}(|\omega|/\pi^2 H(\omega) Q(\omega, \theta) + C(\omega)) - \pi c(\phi)$ becomes a modified data $\bar{q}(\phi, \theta)$. In this way, modified data $\bar{q}(\phi, \theta)$ can be obtained also in the second embodiment by using a proper filtering function $H(\omega)$, function $C(\omega)$ and function $c(\phi)$ and can serve to form a clear-cut and accurate tomographic display.

Instead of the scanner 20, which is usually used in the computed tomography apparatus of the third generation, this invention may use a scanner of the fourth generation which includes a plurality of X-ray sources.

What is claimed is:

1. Apparatus for controlling a display device to display a tomograph of a selected subject, comprising:
    scanner means for orbitally scanning said subject in a specific plane, said scanner means including a radiation source for emitting a fan-shaped X-ray beam and a detector unit for receiving said fan-shaped beam and producing a plurality of detection signals representing X-ray absorption data for portions of said subject within said beam, each of said detection signals being generated by a narrow beam segment of said fan-shaped beam;
    means for converting said detection signals into back-projection signals representing X-ray absorption data which is back-projected onto a reference line in said specific plane according to the distance between said radiation source and said reference line; and
    means for obtaining, according to the distance between said radiation source and said reference line and the distance between said reference line and a given point of the subject within said specific plane, output data signals each representing the contribution of said back-projection signals to the radiation absorption coefficient value of said given point and for adding up the output data signals thus obtained to determine the radiation absorption coefficient values for said point.

2. The apparatus according to claim 1, wherein said means for converting includes means for conducting Fourier series expansion on a low pass filtering function, and means for convolving said detection signals and the output of said means for conducting Fourier series expansion.

3. The apparatus according to claim 1, wherein said means for converting includes means for conducting Fourier transformation on said detection signals, means for applying a low pass filtering function to the output data of said means for conducting Fourier transformation, and means for conducting Fourier inverse transformation on the output data of said means for applying said low pass filtering function.

4. Apparatus for generating radiation absorption data for controlling a display device to display a tomograph of a selected subject comprising:
    scanner means for orbitally scanning said subject in a selected plane, said scanner means including a radiation source for projecting a plurality of radiation beams at diverging angles through said selected plane and a detector unit for detecting said beams and producing a plurality of detection signals representing radiation absorption data for said subject;
    modification means for processing said detection signals with a filtering function to produce modified detection signals;
    back-projection means for processing said modified detection signals to produce back-projection signals representing radiation absorption data for a plurality of first pixels located on a reference line in a pixel matrix in said selected plane; and
    contribution means for processing said back-projection signals to produce contribution signals representing radiation absorption data for pixels in said matrix other than said first pixels, said contribution means including interpolation means for deriving from said back-projection signals an interpolated back-projection signal for each of said other pixels by determining, for each said other pixel, the point where a line extending between said radiation source and said other pixel intersects said reference line and further including means for factoring the value represented by the interpolated back-projection signal for each said other pixel by the ratio $R_a^2/R_b^2$ where $R_a$ represents the perpendicular distance between said reference line and said radiation source and $R_b$ represents the perpendicular distance between said radiation source and a line extending through said other pixel and parallel to said reference line.

5. The apparatus set forth in claim 4 further comprising accumulation means for summing said contribution signals for each pixel in said pixel matrix to provide pixel data signals for controlling said display device to display said tomograph.

6. The apparatus set forth in claim 4 wherein said pixel matrix is referenced to an X-Y coordinate system and said reference line coincides with the X axis thereof and wherein said interpolation means determines said reference line intersection point for each of said other pixels in accordance with the formula $$\beta(o, y) + (R_o/R_y)x$$

where $\beta$ (o, y) represents the point of intersection on said X axis of a line connecting said radiation source and the X-Y coordinate point (o, y), where y represents the Y coordinate of the pixel, x represents the X coordinate of said pixel, $R_o$ represents the perpendicular distance between said radiation source and said X axis, and $R_y$ represents the perpendicular distance between said radiation source and a line, parallel to said X axis, extending through said pixel.

7. The apparatus set forth in claim 4 wherein said pixel matrix is referenced to an X-Y coordinate system and said reference line coincides with the Y axis thereof and wherein said interpolation means determines said reference line intersection point for each of said other pixels in accordance with the formula $$\beta'(x, o) + (R_o/R_x) Y$$

where $\beta'$ (x, o) represents the point of intersection on said Y axis of a line connecting said radiation source and the X-Y coordinate point (x, o), where x represents the X coordinate of the given pixel, y represents the Y coordinate of said pixel, $R_o$ represents the perpendicular distance between said radiation source and said Y axis, and $R_x$ represents the perpendicular distance between said radiation source and a line, parallel to said Y axis, extending through said pixel.

8. The apparatus set forth in claim 4 wherein said back-projection means includes means for deriving from said modified detection signals a set of interpolated modified detection signals representing radiation absorption data for paths in said selected plane defined by a set of lines extending from said radiation source through said first pixels and includes further means for processing each said interpolated modified detection signal with a distance factor signal proportional to the distance from said radiation source to said first pixel for which said interpolated modified detection signal is derived.

9. The apparatus set forth in claim 8 wherein said distance factor signal represents the square of the distance from said radiation source to said first pixel and said further means operates to divide each said interpolated modified detection signal by the distance factor signal for a different one of said first pixels.

* * * * *